United States Patent
Wagner

(10) Patent No.: US 10,471,290 B1
(45) Date of Patent: Nov. 12, 2019

(54) METHOD AND SYSTEM FOR TRAINING ATHLETES BASED ON ATHLETIC SIGNATURES AND PRESCRIPTION

(71) Applicant: SPARTA SOFTWARE CORPORATION, Menlo Park, CA (US)

(72) Inventor: Phillip Patrick Wagner, Menlo Park, CA (US)

(73) Assignee: SPARTA SOFTWARE CORPORATION, Menlo Park, CA (US)

( * ) Notice: Subject to any disclaimer, the term of this patent is extended or adjusted under 35 U.S.C. 154(b) by 0 days.

(21) Appl. No.: 14/050,735

(22) Filed: Oct. 10, 2013

(51) Int. Cl.
*A63B 5/00* (2006.01)
*A63B 24/00* (2006.01)

(52) U.S. Cl.
CPC .......... *A63B 5/00* (2013.01); *A63B 24/0075* (2013.01)

(58) Field of Classification Search
CPC .............. A61B 5/11; A61B 2503/10; A63B 2024/0065; A63B 2220/51; A63B 5/00; A63B 2024/0009
See application file for complete search history.

(56) References Cited

U.S. PATENT DOCUMENTS

| | | | | |
|---|---|---|---|---|
| 2009/0062627 | A1* | 3/2009 | Younger | 600/301 |
| 2009/0069722 | A1* | 3/2009 | Flaction et al. | 600/587 |
| 2010/0317489 | A1* | 12/2010 | Flaction | 482/9 |
| 2012/0023163 | A1* | 1/2012 | Mangold | 709/203 |
| 2012/0071733 | A1* | 3/2012 | Grey et al. | 600/301 |
| 2013/0079907 | A1* | 3/2013 | Homsi et al. | 700/91 |

OTHER PUBLICATIONS

Mizuguchi, Satoshi, "Net Impulse and Net Impulse Characteristics in Vertical Jumping" (2012). Electronic Theses and Dissertations. Paper 1459. http://dc.etsu.edu/etd/1459.*

* cited by examiner

Primary Examiner — Sundhara M Ganesan
(74) Attorney, Agent, or Firm — One LLP

(57) ABSTRACT

A method for training athletes is disclosed. The method comprises: calculating an athletic signature for an athlete comprising normalized values for the concentric net vertical impulse (CON-IMP), the average eccentric rate of force development (ECC-RFD), and the average vertical concentric force (CON-VF) for the athlete; analyzing the athletic signature; and assigning at least one training block to the athlete based on the analysis of the athletic signature.

16 Claims, 16 Drawing Sheets

| | A | B | C | D | E | F | G |
|---|---|---|---|---|---|---|---|
| 1 | class | label | diagnosed via | genetics/ethnic/trait background | sport/position correlation | injury risk | exercise needs |
| 2 | | | | | | | |
| 3 | Athletic Movement Signatures | rotational | explode<5 from others | caucasian, higher body fat | pitcher, quarterback, wide receiver, rugby fullback/wing | limited | core stability |
| 4 | | linear | load<5 from others | ectomorph, lanky | | limited | squat, quick jumps |
| 5 | | | drive<5 from others | mesomorph, african american, polynesian | running back, soccer, any defensive specialist | | center of pressure awareness of arch rather than forefoot |
| 6 | | lateral | | | offensive lineman, front row rugby, baseball catcher | limited | longer movements to prolong and absorb forces |
| 7 | Extreme Movement Signatures | extreme load | load>10 from others | massive body mass, endomorph, excessive upper body and core stability emphasis | | twisting injuries-acl and foot | full range of motion, lower body emphasis |
| 8 | | extreme explode | explode>10 from others | | basketball, tight ends | back injuries twisting back injuries (vertebrae, ligament) | eccentric strength upper body and squats (heavy) |
| 9 | | extreme drive | drive>10 from others | females, asian | volleyball | lower hamstring and upper body | |
| 10 | Weak Movement Signatures | weak load | load<10 from others | over trained, limited use of ankles | basketball | lumbopelvix hip (sports hernia) | squats limited range of motion with higher loads |
| 11 | | weak explode | explode<10 from others | no heavy or intense, quick training/sport | baseball pitchers | | |
| 12 | | weak drive | drive<10 from others | all heavy, no prolonged movements | football, university athletes | muscle strains | glute/hamstring strength |

FIG. 13

METHOD AND SYSTEM FOR TRAINING ATHLETES BASED ON ATHLETIC SIGNATURES AND PRESCRIPTION

FIELD

Embodiments of the present invention relate to athletic performance. In particular, embodiments of the present invention relate to systems for analyzing athletic movement

BACKGROUND

A force plate may be used to generate data relating to athletic movement, e.g. in the form of a jump. However, the data can be quite voluminous as a data point may be generated once every millisecond. This makes analysis of the data difficult.

SUMMARY

According to a first aspect of the invention, a method for training athletes is disclosed. The method comprises: calculating an athletic signature for an athlete comprising normalized values for the concentric net vertical impulse (CON-IMP), the average eccentric rate of force development (ECC-RFD), and the average vertical concentric force (CON-VF) for the athlete; analyzing the athletic signature; and assigning at least one training block to the athlete based on the analysis of the athletic signature.

Other aspects of the invention will be apparent from the detailed description below.

BRIEF DESCRIPTION OF THE FIGURES

FIG. 13 shows an example of guidance, in accordance with one embodiment of the invention.

DETAILED DESCRIPTION

In the following description, for purposes of explanation, numerous specific details are set forth in order to provide a thorough understanding of the invention. It will be apparent, however, to one skilled in the art that the invention can be practiced without these specific details. In other instances, structures and devices are shown in block or flow diagram form only in order to avoid obscuring the invention.

Reference in this specification to "one embodiment" or "an embodiment" means that a particular feature, structure, or characteristic described in connection with the embodiment is included in at least one embodiment of the invention. The appearance of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Moreover, although the following description contains many specifics for the purposes of illustration, anyone skilled in the art will appreciate that many variations and/or alterations to the details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

Figure 1:
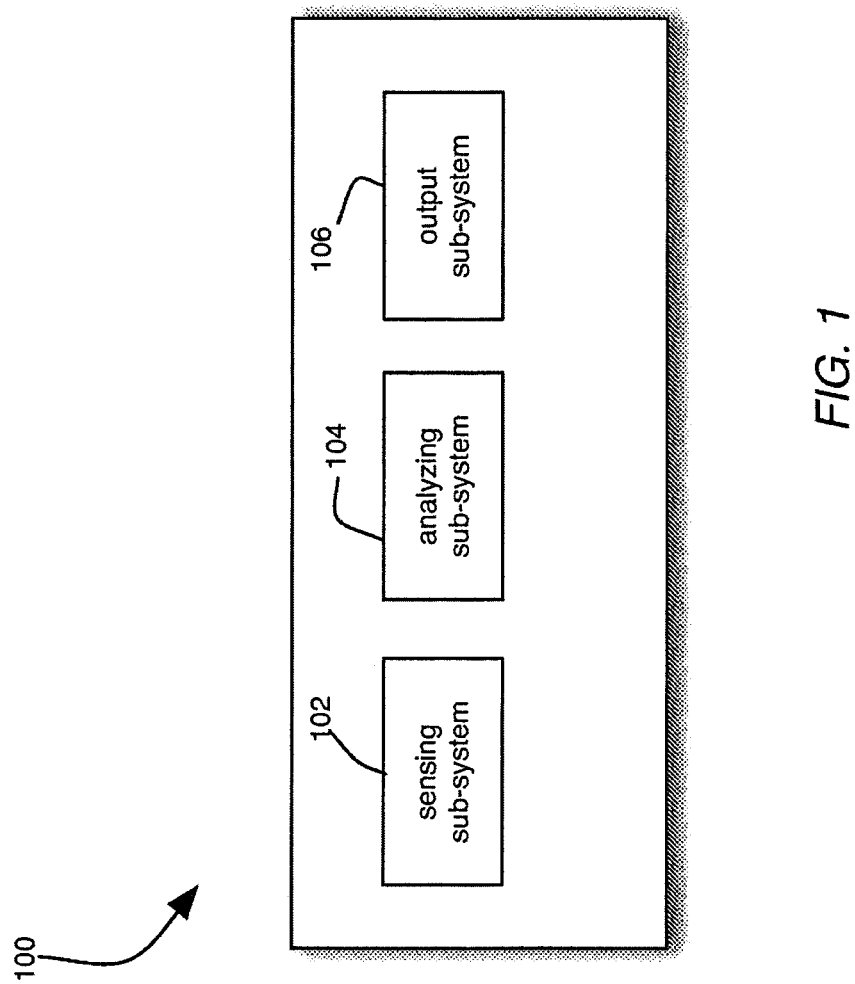
FIG. 1 shows a logical block diagram of a system to analyze athletic movement, in accordance with one embodiment of the invention.

Referring to FIG. 1, embodiments of the present invention disclose a system 100 for analyzing athletic movement. For illustrative purposes, consider the athletic movement to be a vertical jump. However, it is to be understood that the system may be used to analyze other forms of athletic movement, such as golf and baseball swings, baseball and football throws, sprinting, agility, basketball shooting, and kicking.

The system 100 may, at least logically, be divided into a sensing sub-system 102, an analytical sub-system 104, and an output sub-system 106.

Figure 2:
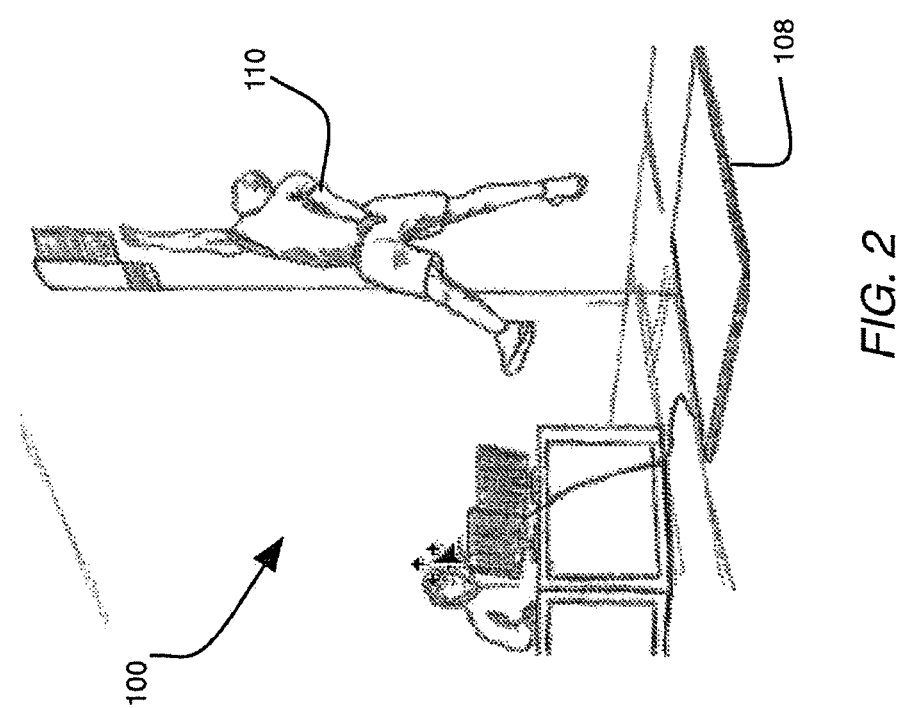
FIG. 2 shows the system of FIG. 1 implemented with a force-plate, in accordance with one embodiment of the invention.

The sensing sub-system 102 may include sensors for sensing a time-dependent variable that changes during the athletic movement. In one embodiment, the sensing sub-system 102 may include a sensor in the form of a force-plate 108, as shown in FIG. 2. In other embodiments, the sensing sub-system 102 may include other types of sensors. For example, in one embodiment, the sensing sub-system 102 may include an accelerometer, which may be integrated, for example, into a bracelet or a shoe pod. In use, an athlete 110 initiates a vertical jump (athletic movement) on the force-plate 108. The force plate 108 records changes in force over time (typically one force reading is captured each millisecond). An analog-to-digital converter (not shown) converts the analog force signal into a digital signal for analysis by the analytical sub-system 104.

The analytical sub-system 104 may include instructions to process the digital signal in order to compile an athletic signature for the athlete 110. In one embodiment, the analytical sub-system 104 extracts selected portions of a force-time curve output by the sensing sub-system 102. Said selected portions may comprise phases of the jump including a load phase, an explode phase, and a drive phase, as detailed below:

(a) load phase: comprises data relating to the average eccentric rate of force development during the jump.

(b) explode phase: comprises data relating to the average relative concentric peak force generated during the jump, computed as average concentric peak force divided by the athlete's weight.

(c) drive phase: comprises data relating to the concentric relative impulse for the jump.

Typically, the system 100 is configured to process a plurality of jumps for each athlete and to store data for each athlete in the form of an athletic signature Each athletic signature may by used to profile an athlete in terms of at least suitability for a given sport, proneness to injury, suitability for particular athletic gear (e.g. shoes), etc.

Figure 3A:
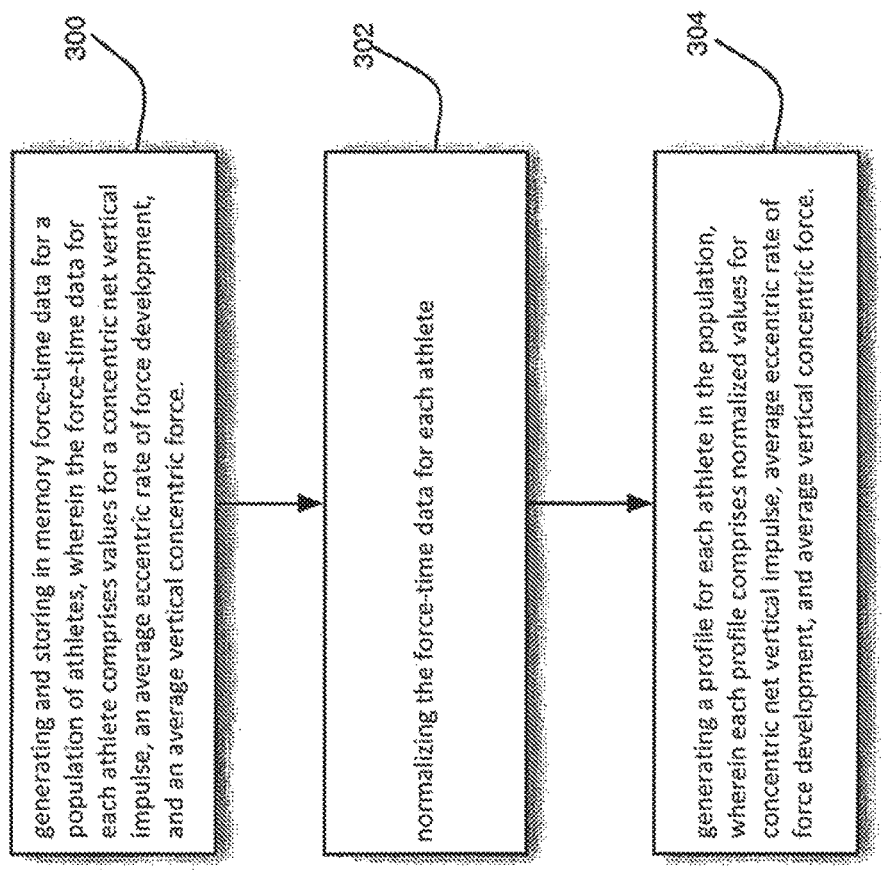
FIGS. 3A and 3B show, respectively, a flowchart of a method for generating a signature for an athlete, and a flowchart of a training method for athletes, each in accordance with one embodiment of the invention.

The output sub-system 106 facilitates output of athletic signatures via printout, display, etc. FIG. 3A shows a flowchart corresponding to a method for generating a signature for an athlete, in accordance with one embodiment. The method includes the following processing blocks.

Block 300: in this block force-time data for a population of athletes is stored in memory. Said force-time data may be generated by a sensing sub-system 102 in respect of each of said plurality of athletes in response to the said athlete performing an athletic movement, and comprises values for a concentric net vertical impulse (CON-IMP), an average eccentric rate of force development (ECC-RFD), and an average vertical concentric force (CON-VF);

Block 302: in this block a normalization of the force-time data for each athlete based on values of the force-time data within the population of athletes is performed;

Block 304: in this block a profile comprising an athletic signature for each athlete in the population is generated, wherein said profile comprises the normalized values for the concentric net vertical impulse (CON-IMP), the average eccentric rate of force development (ECC-RFD), and the average vertical concentric force (CON-VF) for the athlete.

In one embodiment, performing the normalization comprises calculating a T-score for concentric net vertical impulse (CON-IMP), average eccentric rate of force development (ECC-RFD), and average vertical concentric force (CON-VF) for each athlete. Each T-score may be calculated as an average over a standard deviation.

In one embodiment, the population of athletes may comprise athletes who play a particular sport.

In one embodiment, the population of athletes may comprise athletes who play a particular position within a particular sport.

The method may further comprise analyzing the athletic signatures of elite athletes and characterizing said signatures into an archetypal signature corresponding to one of a role within a sport and a sport.

In one embodiment, the force-time data comprises repeating data collected for each athlete when performing the same athletic movement at different times.

Figure 3B:
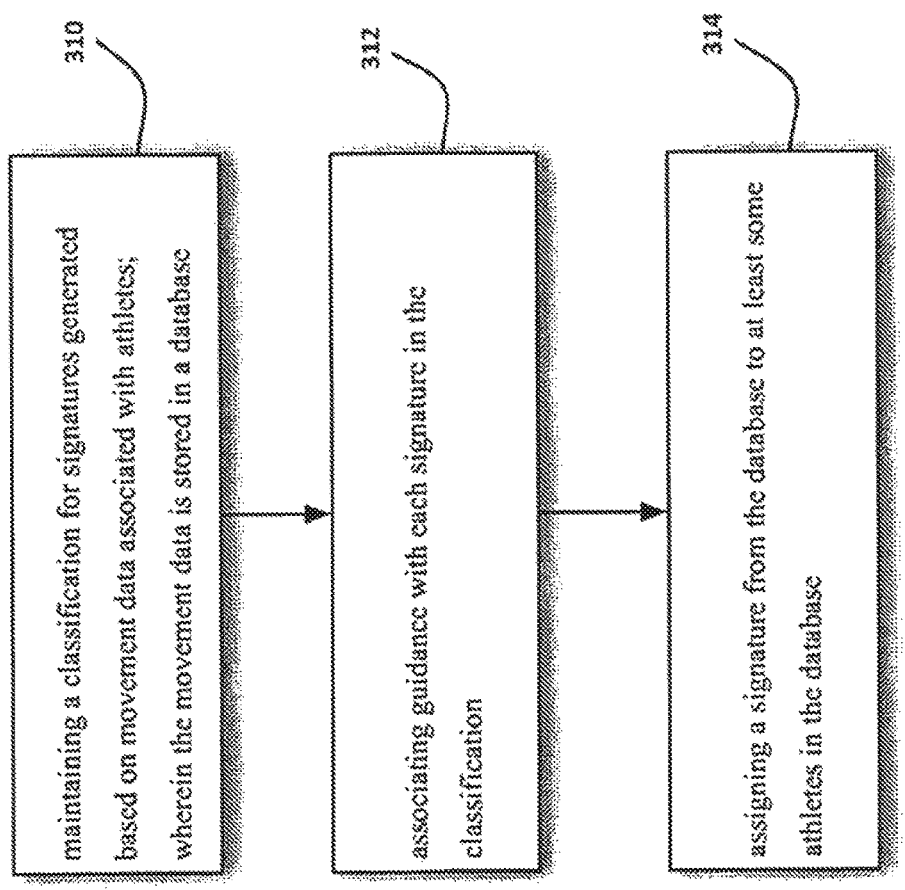

FIG. 3B shows a flowchart of a training method for training athletes, in accordance with one embodiment of the invention. The training method includes the following processing blocks:

Block 310: in this block a classification for signatures generated based on movement data associated with athletes is maintained;

Block 312: in this block guidance is associated with each signature in the classification;

Block 314: in this block a signature is assigned from the database to at least some athletes in the database.

Figure 4:
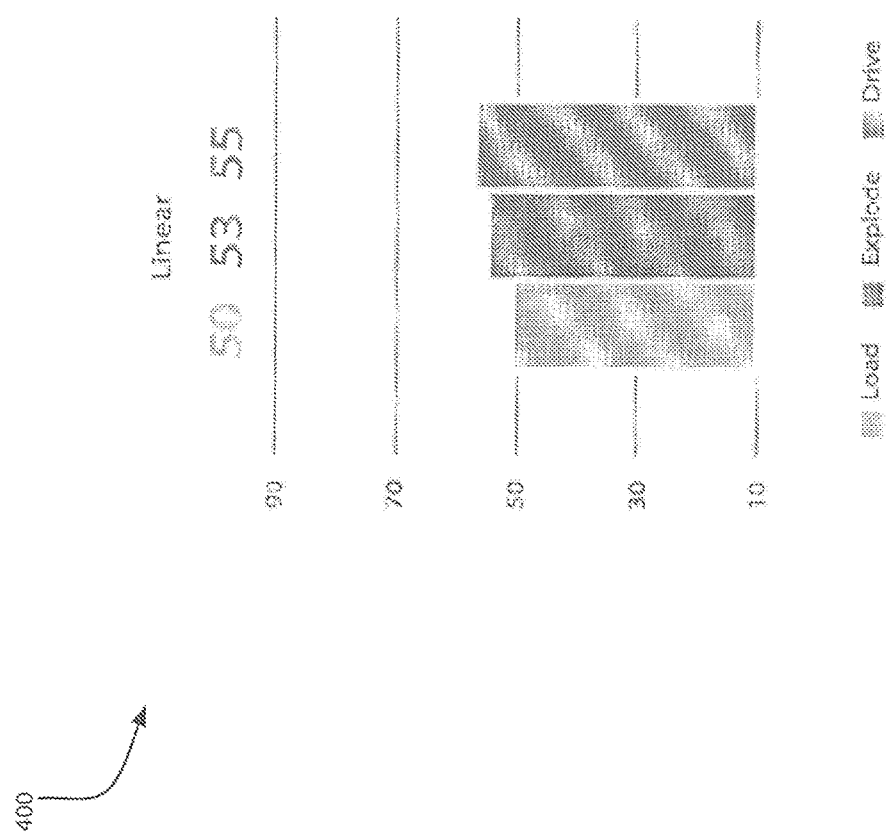
FIG. 4-12 show examples of signatures, in accordance with one embodiment of the invention.

In one embodiment, the classification comprises a linear signature to characterize athletes who excel at movement in a straight line. FIG. 4 shows a depiction of the linear signature in the form of a bar chart 400 to show the values for the variables load, explode, and drive, in accordance with one embodiment. For the linear signature, the load value is less than the others by 5, in one embodiment.

Figure 5:
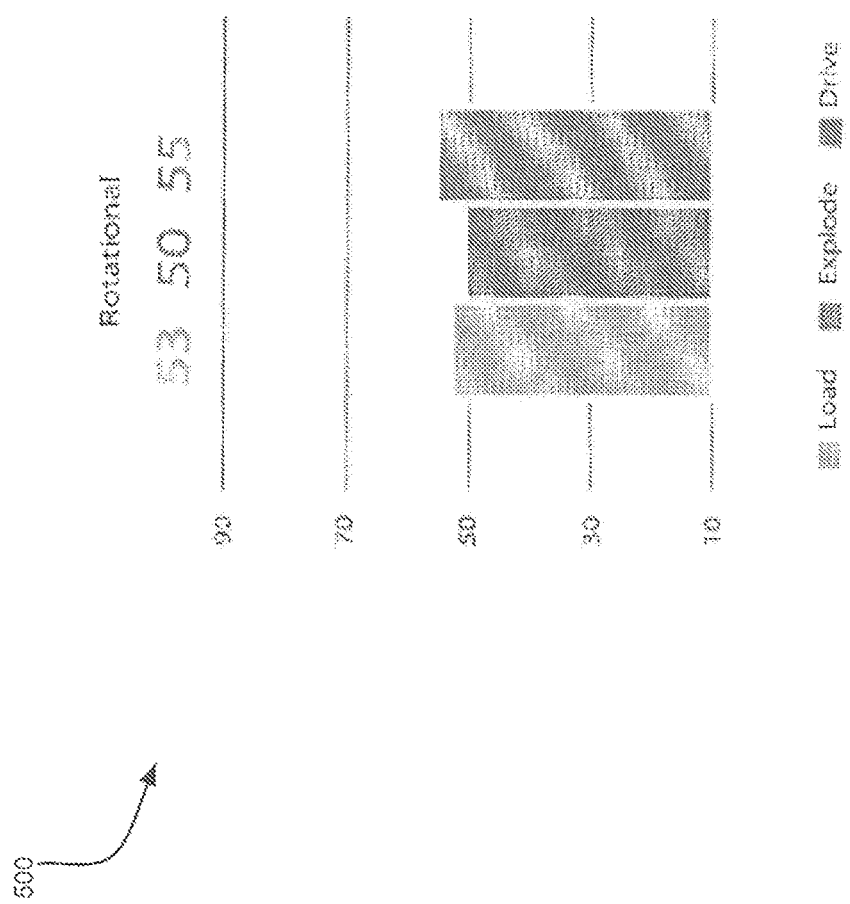

In one embodiment, the classification comprises a rotational signature to characterize athletes who excel at movement that includes an element of rotation. FIG. 5 shows the depiction of the rotational signature in the form of a bar chart 500, in accordance with one embodiment. For the rotational signature, the explode values is less than the others by 5, in one embodiment.

Figure 6:
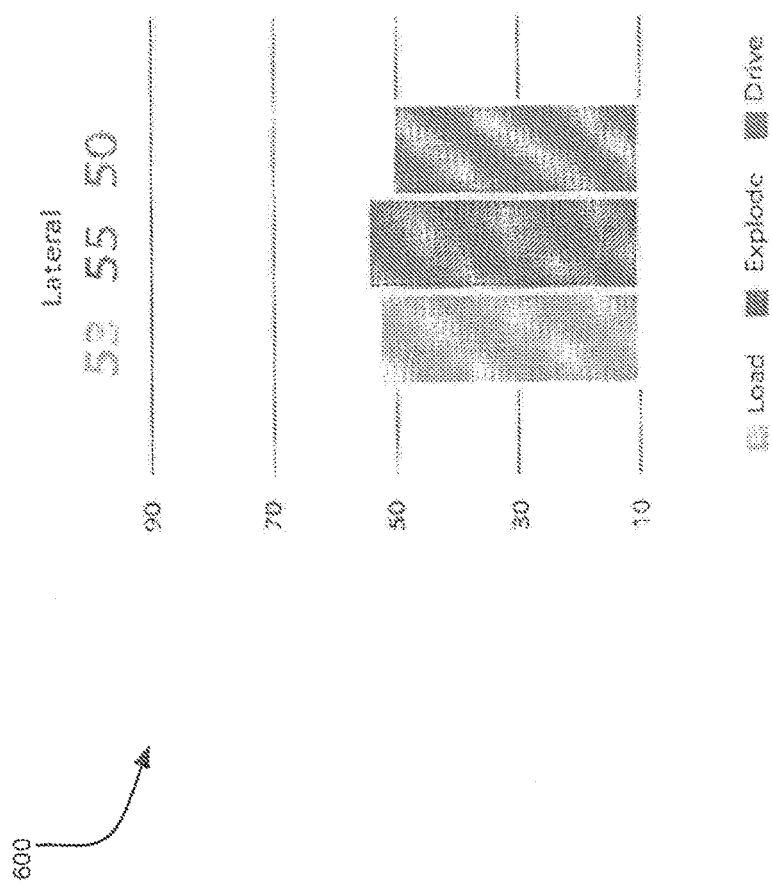

In one embodiment, the classification comprises a lateral signature to characterize athletes who excel at lateral movements. FIG. 6 shows a depiction of the lateral signature in the form of a bar chart 600, in accordance with one embodiment. For the lateral signature, the drive value is less than the others by 5, in one embodiment.

In one embodiment, the classification may include extreme signatures. These are signatures where one of the variables load, explode, drive are higher than the other two by a threshold amount.

Figure 7:
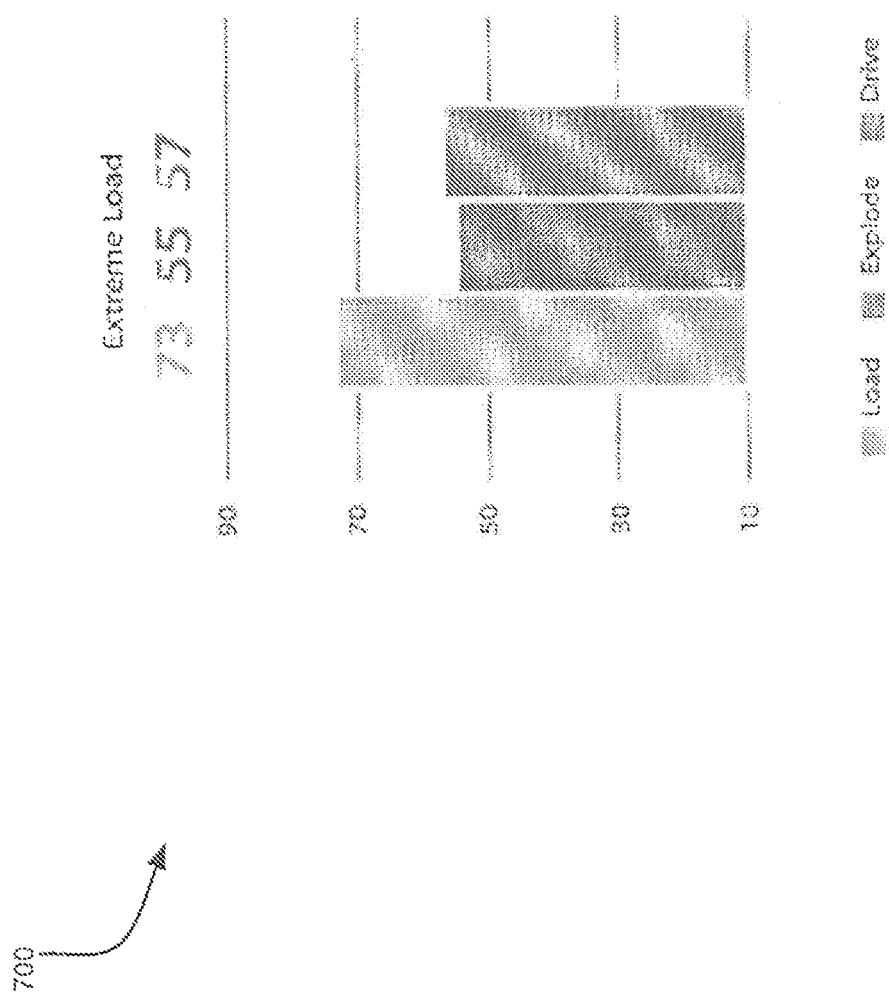

FIG. 7 shows a bar chart 700 corresponding to a signature classification called extreme load for which the load value exceeds the other values by 10.

Figure 8:
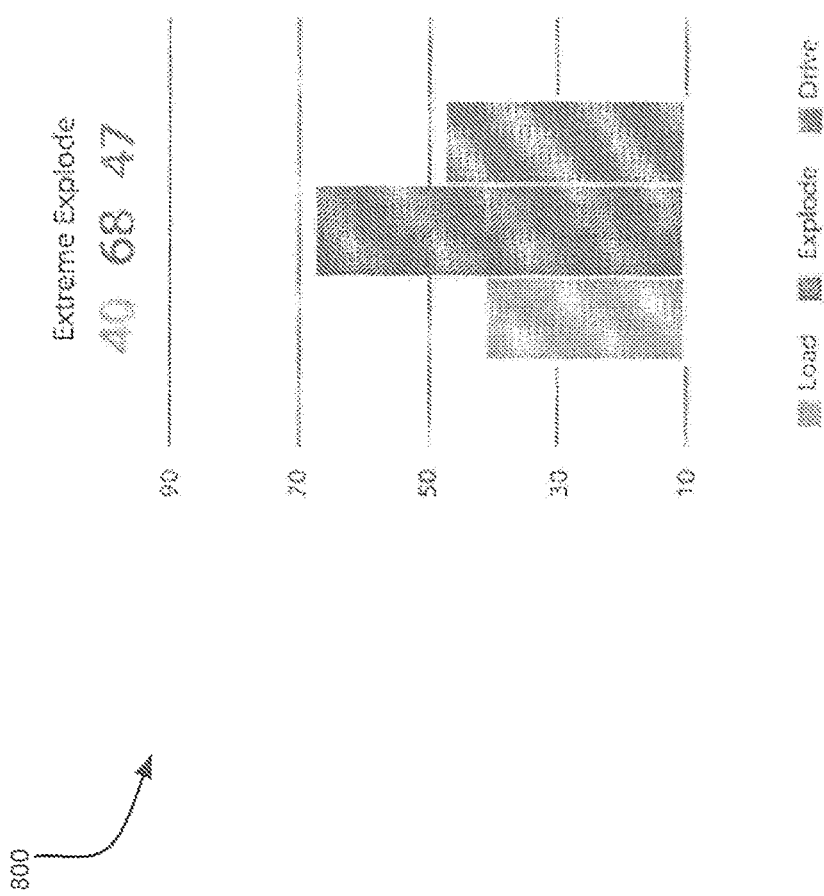

FIG. 8 shows a bar chart 800 corresponding to a signature classification called extreme explode for which the explode value exceeds the other values by 10.

Figure 9:
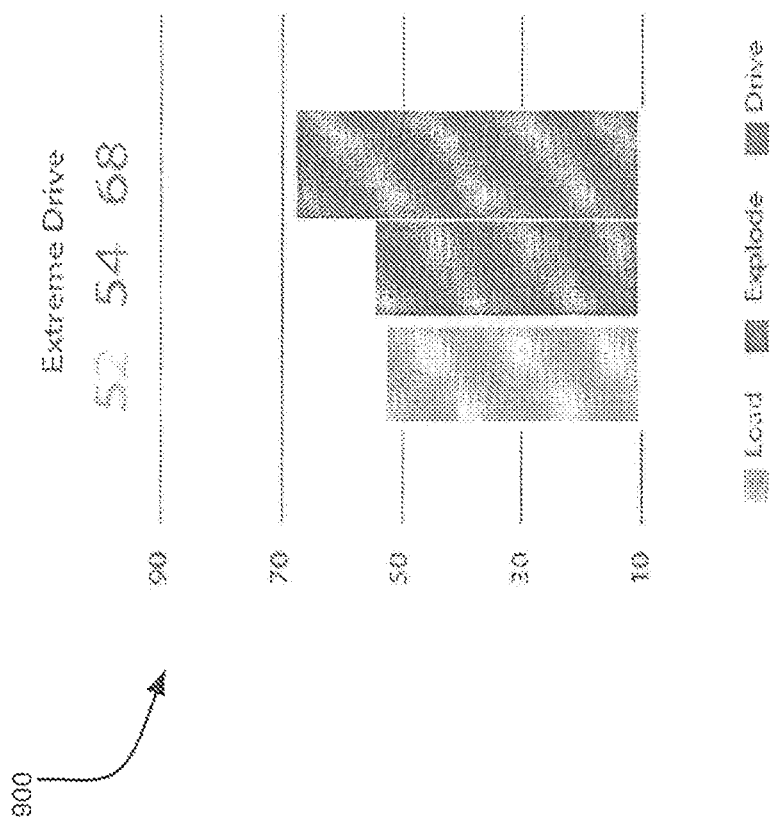

FIG. 9 shows a bar chart 900 corresponding to a signature classification called extreme drive for which the drive value exceeds the other values by 10.

In one embodiment, the classification may include weak signatures. These are signatures where one of the variables load, explode, drive is lower than the other two by a threshold amount.

Figure 10:
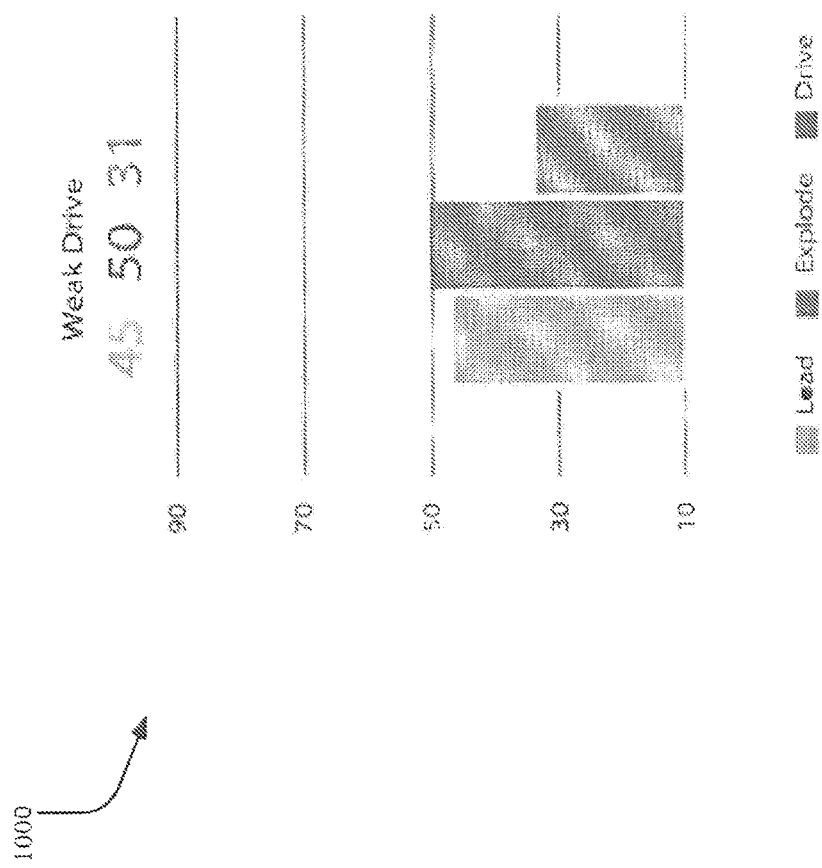

FIG. 10 shows a bar chart 1000 corresponding to a signature classification called weak drive for which the drive value is less than the other values by 10.

Figure 11:
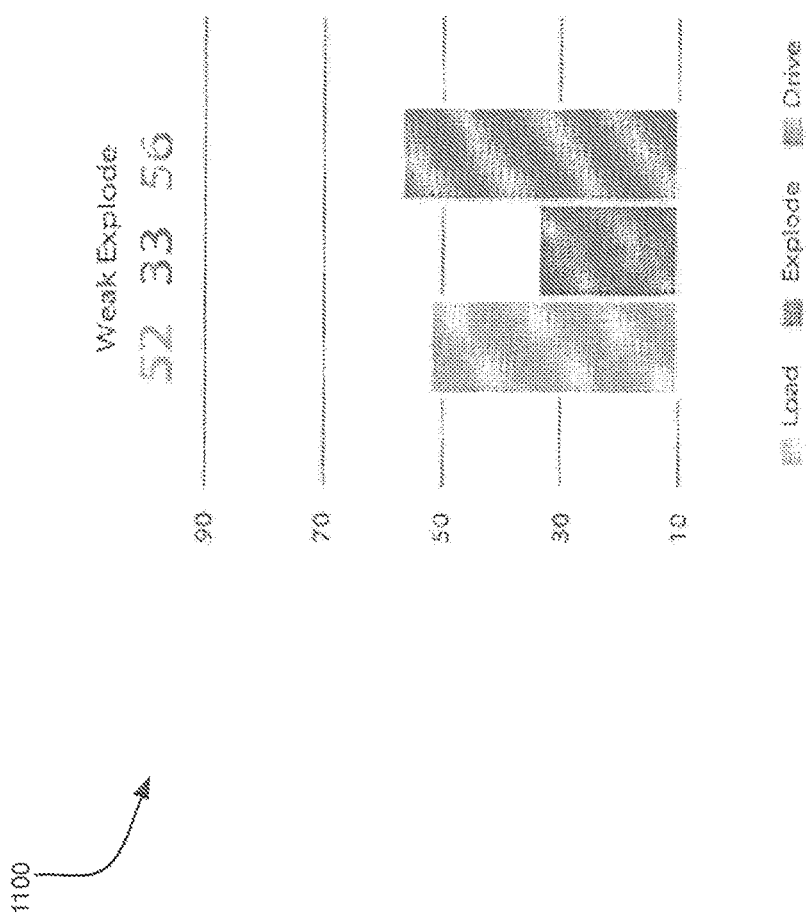

FIG. 11 shows a bar chart 1100 corresponding to a signature classification called weak explode for which the explode value is less than the other values by 10.

Figure 12:
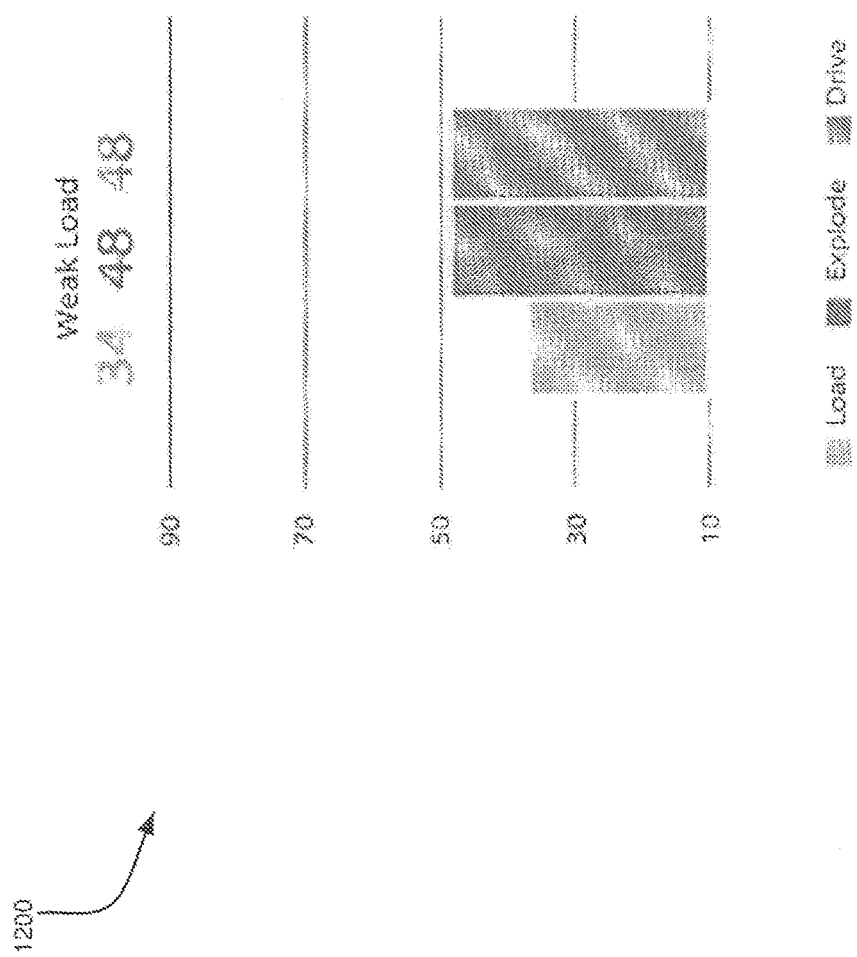

FIG. 12 shows a bar chart 1200 corresponding to a signature classification called weak load for which the load value is less than the other values by 10.

FIG. 13 shows a matrix 1300 indicative of the type of guidance that might be associated with the signatures in the classification, in accordance with one embodiment. As will be seen the matrix 1300 associates particular signatures with genetic/ethnic background, sport, position in sport, injury risk, and exercise needs.

In one embodiment, by determining signatures for athletes that are good at certain sports or certain positions within sports it is possible to determine certain archetypical signatures associated with performance excellence. Column E in the matrix 1300 indicates the archetypical signatures for certain sports, and sport positions.

In one embodiment, the guidance may comprise at least one exercise protocol for at least one of transforming an athlete's signature to a desired signature and preventing injury to the athlete. The exercise protocol may comprise an exercise definition, a number of repetitions associated with the exercise, a number of sets associated with the exercise, and a schedule for performing the exercise.

The output sub-system 106 facilitates output of athletic signatures via printout, display, etc.

In one embodiment, the athletic signatures may be used to train athletes based on a prescription. Elements of a prescription may include:

a) a movement, e.g. a squat;
b) an exercise, e.g., 18" box squat;
c) a method for performing an exercise. For example, in on embodiment, the method for performing the exercise may specify a loading scheme for the exercise which includes the number of repetitions to be performed, the speed at which each repetition is to be performed, and a weight associated with each exercise;

d) one or more performance targets for an athlete. Each performance target may define an achievement/milestone of an athlete that signifies an aspect of athletic proficiency or competence.

Figure 14:
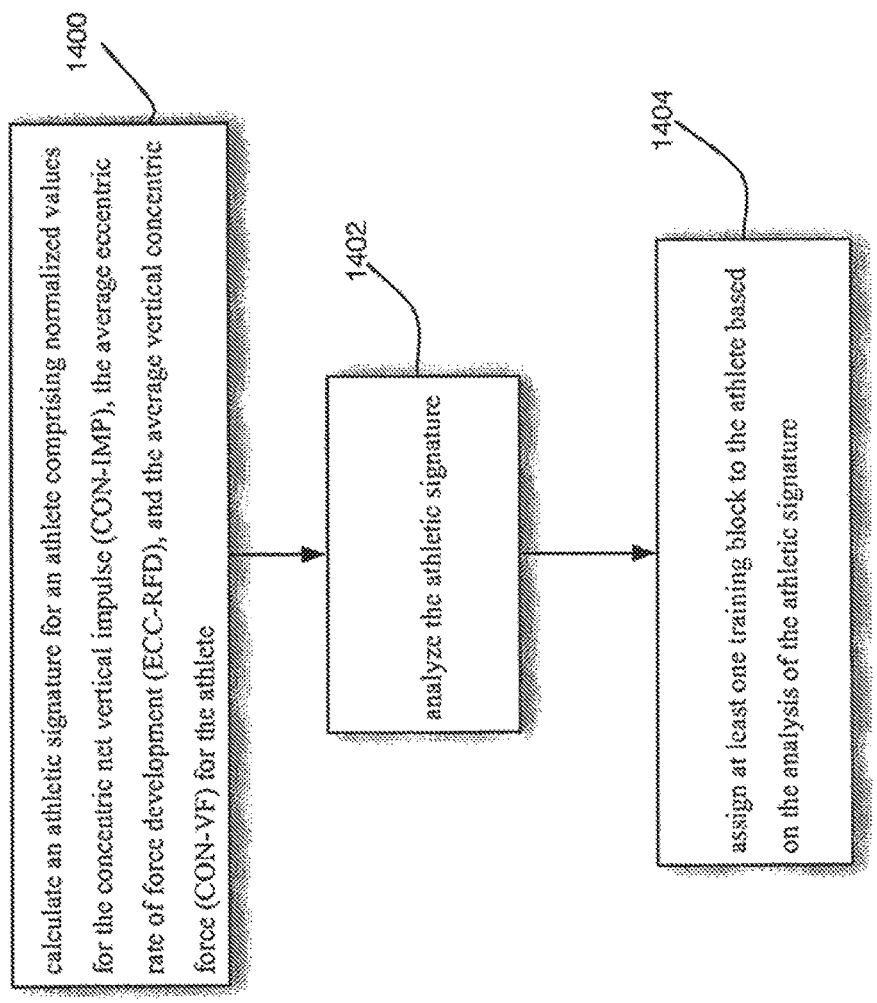
FIG. 14 shows of a method for training athletes based on signatures and prescriptions, in accordance with one embodiment of the invention.

FIG. 14 shows the steps for a training method based on signatures and prescriptions. Referring to FIG. 14 at block 1400, a signature for an athlete is calculated in accordance with the techniques already disclosed herein. Each signature includes three variables. These are the normalized values for the concentric net vertical impulse (CON-IMP), the average eccentric rate of force development (ECC-RFD), and the average vertical concentric force (CON-VF) for the athlete.

At block 1402, the signature is analyzed. In one embodiment, this analysis may include a calculation of the relative differences in the three variables in the signature. Statistical techniques may be used to analyze the relative differences in the three variables in an athlete's signature for a whole population of athletes. Thus, significant differences in the three variables may be identified and associated with particular prescriptions. Each prescription may be designed to improve a particular aspect of an athlete's performance.

At block 1404, at least one training block may be assigned to the athlete based on the analysis of the athletic signature. In the case of more than one block, the blocks may be prioritized. Each block may comprise more than one prescription.

For example, the analysis step may reveal that for a particular athlete, the value for load is 8 less than the values for explode and drive. This condition may requires 2 "doses" of a exercise in a prescription, whereas if the value for load was only 4 less than the values for explode and drive, then the prescription may only specify a dosage of only 1 for the exercise Embodiments of the invention also monitor the "consumption" of a prescription. For example, an athlete may use an app on a smartphone to input data about the prescriptions taken by the athlete. This data is collected and analyzed to determine an efficacy of a prescription and/or a dosage, and may be used to calculate changes in a prescription or dosage. In one embodiment, the data input allows calculation of exercise changes over time, which are then correlated with movement signature changes and sport statistical changes (e.g., yards rushing, receptions, etc.).

Figure 15:
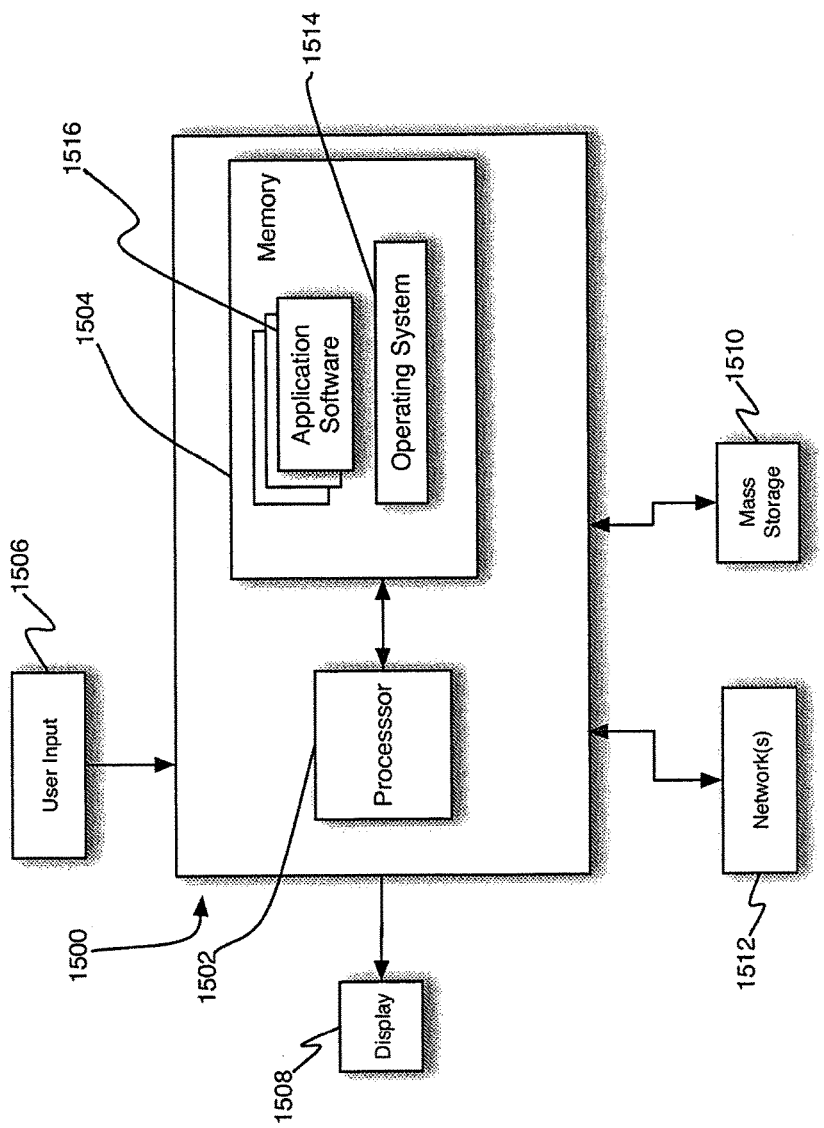
FIG. 15 shows a high-level block diagram of hardware used to implement the system of FIG. 1, in accordance with one embodiment of the invention.

FIG. 15 shows an example of hardware 1500 that may be used to implement portions of the system 100, in accordance with one embodiment. The hardware 1500 may include at least one processor 1502 coupled to a memory 1504. The processor 1502 may represent one or more processors (e.g., microprocessors), and the memory 1504 may represent random access memory (RAM) devices comprising a main storage of the hardware, as well as any supplemental levels of memory, e.g., cache memories, non-volatile or back-up memories (e.g., programmable or flash memories), read-only memories, etc. In addition, the memory 1504 may be considered to include memory storage physically located elsewhere in the hardware, e.g., any cache memory in the processor 1502, as well as any storage capacity used as a virtual memory, e.g., as stored on a mass storage device.

The hardware also typically receives a number of inputs and outputs for communicating information externally. For interface with a user or operator, the hardware may include one or more user input/output devices 1506 (e.g., force-plate, keyboard, mouse, etc.) and a display 1508. For additional storage, the hardware 1500 may also include one or more mass storage devices 1510, e.g., a Universal Serial Bus (USB) or other removable disk drive, a hard disk drive, a Direct Access Storage Device (DASD), an optical drive (e.g., a Compact Disk (CD) drive, a Digital Versatile Disk (DVD) drive, etc.) and/or a USB drive, among others. Furthermore, the hardware may include an interface with one or more networks 1512 (e.g., a local area network (LAN), a wide area network (WAN), a wireless network, and/or the Internet among others) to permit the communication of information with other computers coupled to the network. It should be appreciated that the hardware typically includes suitable analog and/or digital interfaces between the processor 1502 and each of the components, as is well known in the art.

The hardware 1500 operates under the control of an operating system 1514, and executes application software 1516 which includes various computer software applications, components, programs, objects, modules, etc. to perform the techniques described above.

In general, the routines executed to implement the embodiments of the invention, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processors in a computer, cause the computer to perform operations necessary to execute elements involving the various aspects of the invention. Moreover, while the invention has been described in the context of fully functioning computers and computer systems, those skilled in the art will appreciate that the various embodiments of the invention are capable of being distributed as a program product in a variety of forms, and that the invention applies equally regardless of the particular type of machine or computer-readable media used to actually effect the distribution. Examples of computer-readable media include but are not limited to recordable type media such as volatile and non-volatile memory devices, USB and other removable media, hard disk drives, optical disks (e.g., Compact Disk Read-Only Memory (CD ROMS), Digital Versatile Disks, (DVDs), etc.), flash drives among others.

Although the present invention has been described with reference to specific exemplary embodiments, it will be evident that the various modification and changes can be made to these embodiments without departing from the broader spirit of the invention. Accordingly, the specification and drawings are to be regarded in an illustrative sense rather than in a restrictive sense.

The invention claimed is:

1. A computer-based method for prescribing an exercise protocol to rehabilitate or prevent injury in athletes, comprising:

generating by a sensing sub-system, analog force-time data in response to an athletic movement of an athlete;

converting the analog force-time data into a digital signal using an analog-to-digital converter;

analyzing the digital signal in an analytical sub-system, wherein said analyzing comprises:

extracting a plurality of portions from the digital signal, the extracted portions comprising a plurality of values including a concentric net vertical impulse (CON-IMP), an average eccentric rate of force development (ECC-RFD), and an average vertical concentric force (CON-VF) for the athlete;

generating an athletic signature by normalizing the plurality of values, wherein said normalizing includes calculating a T-score for each of the plurality of values based on a plurality of athletic signatures aggregated in a database;
calculating one or more relative differences between the plurality of normalized values; and
comparing the one or more relative differences with one or more predetermined thresholds to determine a signature classification;
storing the athletic signature and the one or more relative differences in the database;
determining, by one or more processors, a personalized training guidance for the athlete based on the athletic signature and the signature classification, wherein said determining comprises referencing the database, wherein the database further includes training guidance associated with the plurality of athletic signatures, and wherein said personalized training guidance comprises at least one of an exercise definition, a number of repetitions associated with the exercise, a number of sets associated with the exercise, and a schedule for performing the exercise; and
displaying, through a computer program, the personalized training guidance.

2. The method of claim 1 further comprises determining, by one or more processors, at least one prescription.

3. The method of claim 2, wherein each prescription comprises at least a movement and an exercise associated with the movement.

4. The method of claim 3, wherein each prescription comprises a loading scheme for performing the exercise.

5. The method of claim 4, wherein the prescription comprises an achievement target.

6. A non-transitory computer-readable medium comprising instructions which when executed by a processing system causes said system to perform a method for prescribing an exercise protocol to rehabilitate or prevent injury in athletes, comprising:
generating by a sensing sub-system, analog force-time data in response to an athletic movement of an athlete;
converting the analog force-time data into a digital signal using an analog-to-digital converter;
analyzing the digital signal in an analytical sub-system, wherein said analyzing comprises:
extracting a plurality of portions from the digital signal, the extracted portions comprising a plurality of values including a concentric net vertical impulse (CON-IMP), an average eccentric rate of force development (ECC-RFD), and an average vertical concentric force (CON-VF) for the athlete;
generating an athletic signature by normalizing the plurality of values, wherein said normalizing includes calculating a T-score for each of the plurality of values based on a plurality of athletic signatures aggregated in a database;
calculating one or more relative differences between the plurality of normalized values; and
comparing the one or more relative differences with one or more predetermined thresholds to determine a signature classification;
storing the athletic signature and the one or more relative differences in the database;
determining, by one or more processors, a personalized training guidance for the athlete based on the athletic signature and the signature classification, wherein said determining comprises referencing the database, wherein the database further includes training guidance associated with the plurality of athletic signatures, and wherein said personalized training guidance comprises at least one of an exercise definition, a number of repetitions associated with the exercise, a number of sets associated with the exercise, and a schedule for performing the exercise; and
displaying, through a computer program, the personalized training guidance.

7. The computer-readable medium of claim 6 further comprises determining, by one or more processors, at least one prescription.

8. The computer-readable medium of claim 7, wherein each prescription comprises at least a movement and an exercise associated with the movement.

9. The computer-readable medium of claim 8, wherein each prescription comprises a loading scheme for performing the exercise.

10. The computer-readable medium of claim 9, wherein the prescription comprises an achievement target.

11. A system for prescribing an exercise protocol to rehabilitate or prevent injury in athletes, comprising:
a processor; and
a memory coupled to the processor, the memory storing instructions which when executed by the processor, causes the system to:
generate by a sensing sub-system, analog force-time data in response to an athletic movement of an athlete;
convert the analog force-time data into a digital signal using an analog-to-digital converter;
analyze the digital signal in an analytical sub-system, wherein said analyzing comprises:
extracting a plurality of portions from the digital signal, the extracted portions comprising a plurality of values including a concentric net vertical impulse (CON-IMP), an average eccentric rate of force development (ECC-RFD), and an average vertical concentric force (CON-VF) for the athlete;
generating an athletic signature by normalizing the plurality of values, wherein said normalizing includes calculating a T-score for each of the plurality of values based on a plurality of athletic signatures aggregated in a database;
calculating one or more relative differences between the plurality of normalized values; and
comparing the one or more relative differences with one or more predetermined thresholds to determine a signature classification;
store the athletic signature and the one or more relative differences in the database;
determine a personalized training guidance for the athlete based on the athletic signature and the signature classification, wherein said determining comprises referencing the database, wherein the database further includes training guidance associated with the plurality of athletic signatures, and wherein said personalized training guidance comprises at least one of an exercise definition, a number of repetitions associated with the exercise, a number of sets associated with the exercise, and a schedule for performing the exercise; and
display, through a computer program, the personalized training guidance.

12. The system of claim 11, wherein the instructions stored in memory, when executed by the processor, further cause the system to determine at least one prescription.

13. The system of claim 12, wherein each prescription comprises at least a movement and an exercise associated with the movement.

14. The system of claim 13, wherein each prescription comprises a loading scheme for performing the exercise.

15. The system of claim 14, wherein the prescription comprises an achievement target.

16. The system of claim 11, wherein the instructions stored in memory, when executed by the processor, further cause the system to: analyze the athletic signatures of elite athletes and characterize the athletic signatures into an archetypal signature corresponding to one of a role within a sport and a sport.

* * * * *